United States Patent [19]
Peery et al.

[11] Patent Number: 6,136,557
[45] Date of Patent: Oct. 24, 2000

[54] *STREPOCOCCUS PNEUMONIAE* GENE SEQUENCE FTSH

[75] Inventors: Robert Brown Peery, Brownsburg; Paul Luther Skatrud, Greenwood; Q May Wang; Michele Louise Young Bellido, both of Indianapolis, all of Ind.

[73] Assignee: Eli Lilly and Company, Indianapolis, Ind.

[21] Appl. No.: 08/987,123

[22] Filed: Dec. 8, 1997

Related U.S. Application Data

[60] Provisional application No. 60/036,281, Dec. 13, 1996.

[51] Int. Cl.[7] .............................. C07H 21/04; C12N 1/20; C12N 15/63; C12N 15/00
[52] U.S. Cl. ..................... 435/69.1; 435/71.1; 435/220; 435/252.3; 435/320.1; 435/471; 435/212; 536/23.2; 536/23.7; 536/24.32
[58] Field of Search ................................ 435/69.1, 320.1, 435/252.3, 220, 471, 183, 212, 24.32, 71.1; 536/23.2, 23.7

[56] References Cited

U.S. PATENT DOCUMENTS 5,591,839  1/1997  Miller et al. ........................... 536/23.7

OTHER PUBLICATIONS

Toshifumi Tomoyasu, et al. "The *Escherichia coli* FtsH Protein Is a Prokaryotic Member of a Protein Family of Putative ATPase Involved in Membrane Functions, Cell Cycle Control, and Gene Expression." *Journal of Bacteriology* 175(5): 1344–1351 (Mar. 1993).

Simon Cutting, et al. "Spo VM, a Small Protein Essential to Development in *Bacillus subtilis,* Interacts with the ATP–Dependent Protease FtsH." *Journal of Bacteriology* 179(17) :5534–5542 (Sep. 1997).

Toshifumi Tomoyasu, et al. "*Escherichia coli* FtsH is a membrane–bound, ATP–dependent protease which degrades the heat–shock transcription factor $\sigma^{32}$." *The EMBO Journal* 14(11) :2551–2560 (1995).

*Primary Examiner*—Carla J. Myers
*Attorney, Agent, or Firm*—Charles E. Cohen; Thomas D. Webster

[57] ABSTRACT

The invention provides isolated nucleic acid compounds encoding FtsH of *Streptococcus pneumoniae*. Also provided are vectors and transformed host cells for expressing the encoded protein, and a method for identifying compounds that bind and/or inhibit said protein.

27 Claims, No Drawings

SEQUENCE LISTING

<160> NUMBER OF SEQ ID NOS: 4

<210> SEQ ID NO 1
<211> LENGTH: 1959
<212> TYPE: DNA
<213> ORGANISM: Streptococcus pneumoniae
<220> FEATURE:
<221> NAME/KEY: CDS
<222> LOCATION: (1)..(1956)

<400> SEQUENCE: 1

```
atg aaa aaa caa aat aat ggt tta att aaa aat cct ttt cta tgg tta      48
Met Lys Lys Gln Asn Asn Gly Leu Ile Lys Asn Pro Phe Leu Trp Leu
  1               5                  10                  15 tta ttt atc ttt ttc ctt gtg aca gga ttc cag tat ttc tat tct ggg      96
Leu Phe Ile Phe Phe Leu Val Thr Gly Phe Gln Tyr Phe Tyr Ser Gly
             20                  25                  30 aat aac tca gga gga agt cag caa atc aac tat act gag ttg gta caa     144
Asn Asn Ser Gly Gly Ser Gln Gln Ile Asn Tyr Thr Glu Leu Val Gln
         35                  40                  45 gaa att acc gat ggt aat gaa aaa gaa tta act tac caa cca aat gtt     192
Glu Ile Thr Asp Gly Asn Glu Lys Glu Leu Thr Tyr Gln Pro Asn Val
     50                  55                  60 agt gtt atc gaa gtt tct ggt gtc tat aaa aat cct aaa aca agt aaa     240
Ser Val Ile Glu Val Ser Gly Val Tyr Lys Asn Pro Lys Thr Ser Lys
 65                  70                  75                  80 gaa gga aca ggt att cag ttt ttc acg cca tct gtt act aag gta gag     288
Glu Gly Thr Gly Ile Gln Phe Phe Thr Pro Ser Val Thr Lys Val Glu
                 85                  90                  95 aaa ttt acc agc act att ctt cct gca gat act acc gta tca gaa ttg     336
Lys Phe Thr Ser Thr Ile Leu Pro Ala Asp Thr Thr Val Ser Glu Leu
            100                 105                 110 caa aaa ctt gct act gac cat aaa gca gaa gta act gtt aag cat gaa     384
Gln Lys Leu Ala Thr Asp His Lys Ala Glu Val Thr Val Lys His Glu
        115                 120                 125 agt tca agt ggt ata tgg att aat cta ctc gta tcc att gtg cca ttt     432
Ser Ser Ser Gly Ile Trp Ile Asn Leu Leu Val Ser Ile Val Pro Phe
    130                 135                 140 gga att cta ttc ttc cta ttc tct atg atg gga aat atg gga gga         480
Gly Ile Leu Phe Phe Phe Leu Phe Ser Met Met Gly Asn Met Gly Gly
145                 150                 155                 160 ggc aat ggc cgt aat cca atg agt ttt gga cgt agt aag gct aaa gca     528
Gly Asn Gly Arg Asn Pro Met Ser Phe Gly Arg Ser Lys Ala Lys Ala
                165                 170                 175 gca aat aaa gaa gat att aaa gta aga ttt tca gat gtt gct gga gct     576
Ala Asn Lys Glu Asp Ile Lys Val Arg Phe Ser Asp Val Ala Gly Ala
            180                 185                 190 gag gaa gaa aaa caa gaa cta gtt gaa gtt gtt gag ttc tta aaa gat     624
Glu Glu Glu Lys Gln Glu Leu Val Glu Val Val Glu Phe Leu Lys Asp
        195                 200                 205 cca aaa cga ttc aca aaa ctt gga gcc cgt att cca gca ggt gtt ctt     672
Pro Lys Arg Phe Thr Lys Leu Gly Ala Arg Ile Pro Ala Gly Val Leu
    210                 215                 220 ttg gag gga cct ccg ggg aca ggt aag act ttg ctt gct aag gca gtc     720
Leu Glu Gly Pro Pro Gly Thr Gly Lys Thr Leu Leu Ala Lys Ala Val
```

|  |  |  |  |  |  |  |  |  |  |  |  |  |  |  |  |
|---|---|---|---|---|---|---|---|---|---|---|---|---|---|---|---|
| 225 |  |  |  | 230 |  |  |  | 235 |  |  |  | 240 |  |  |  |

```
gct gga gaa gca ggt gtt cca ttc ttt agt atc tca ggt tct gac ttt       768
Ala Gly Glu Ala Gly Val Pro Phe Phe Ser Ile Ser Gly Ser Asp Phe
                245                 250                 255 gta gaa atg ttt gtc gga gtt gga gct agt cgt gtt cgc tct ctt ttt       816
Val Glu Met Phe Val Gly Val Gly Ala Ser Arg Val Arg Ser Leu Phe
                260                 265                 270 gag gat gcc aaa aaa gca gca cca gct atc atc ttt atc gat cta aat       864
Glu Asp Ala Lys Lys Ala Ala Pro Ala Ile Ile Phe Ile Asp Leu Asn
            275                 280                 285 gat gct gtt gga cgt caa cgt gga gtc ggt ctc ggc gga ggt aat gac       912
Asp Ala Val Gly Arg Gln Arg Gly Val Gly Leu Gly Gly Gly Asn Asp
        290                 295                 300 gaa cgt gaa caa acc ttg aac caa ctt ttg att gag atg gat ggt ttt       960
Glu Arg Glu Gln Thr Leu Asn Gln Leu Leu Ile Glu Met Asp Gly Phe
305                 310                 315                 320 gag gga aat gaa ggg att atc gtc atc gct gcg aca aac cgt tca gat      1008
Glu Gly Asn Glu Gly Ile Ile Val Ile Ala Ala Thr Asn Arg Ser Asp
                325                 330                 335 gta ctt gat cct gcc ctt ttg cgt cca gga cgt ttt gat aga aaa gta      1056
Val Leu Asp Pro Ala Leu Leu Arg Pro Gly Arg Phe Asp Arg Lys Val
                340                 345                 350 ttg gtt ggc cgt cct gat gtt aaa ggt cgt gaa gca atc ttg aaa gtt      1104
Leu Val Gly Arg Pro Asp Val Lys Gly Arg Glu Ala Ile Leu Lys Val
                355                 360                 365 cac gct aag aac aag cct tta gca gaa gat gtt gat ttg aaa tta gtg      1152
His Ala Lys Asn Lys Pro Leu Ala Glu Asp Val Asp Leu Lys Leu Val
        370                 375                 380 gct caa caa act cca ggc ttt gtt ggt gct gat tta gag aat gtc ttg      1200
Ala Gln Gln Thr Pro Gly Phe Val Gly Ala Asp Leu Glu Asn Val Leu
385                 390                 395                 400 aat gaa gca gct tta gtt gct gct cgt cgc aat aaa tcg ata att gat      1248
Asn Glu Ala Ala Leu Val Ala Ala Arg Arg Asn Lys Ser Ile Ile Asp
                405                 410                 415 gct tca gat att gat gaa gca gaa gat aga gtt att gct gga cct tct      1296
Ala Ser Asp Ile Asp Glu Ala Glu Asp Arg Val Ile Ala Gly Pro Ser
                420                 425                 430 aag aaa gat aag aca gtt tca caa aaa gaa cga gaa ttg gtt gct tac      1344
Lys Lys Asp Lys Thr Val Ser Gln Lys Glu Arg Glu Leu Val Ala Tyr
                435                 440                 445 cat gag gca gga cat acc att gtt ggt cta gtc ttg tcg act gct cgc      1392
His Glu Ala Gly His Thr Ile Val Gly Leu Val Leu Ser Thr Ala Arg
        450                 455                 460 gtt gtc cat aag gtt aca att gta cca cgc ggc cgt gca ggc gga tac      1440
Val Val His Lys Val Thr Ile Val Pro Arg Gly Arg Ala Gly Gly Tyr
465                 470                 475                 480 atg att gca ctt cct aaa gag gat caa atg ctt cta tct aaa gaa gat      1488
Met Ile Ala Leu Pro Lys Glu Asp Gln Met Leu Leu Ser Lys Glu Asp
                485                 490                 495 atg aaa gag caa ttg gct ggc tta atg ggt gga cgt gta gct gaa gaa      1536
Met Lys Glu Gln Leu Ala Gly Leu Met Gly Gly Arg Val Ala Glu Glu
                500                 505                 510 att atc ttt aat gtc caa act aca gga gct tca aac gac ttt gaa caa      1584
Ile Ile Phe Asn Val Gln Thr Thr Gly Ala Ser Asn Asp Phe Glu Gln
                515                 520                 525 gcg aca caa atg gca cgt gca atg gtt aca gag tac ggt atg agt gaa      1632
Ala Thr Gln Met Ala Arg Ala Met Val Thr Glu Tyr Gly Met Ser Glu
        530                 535                 540 aaa ctt ggc cca gta caa tat gaa gga aac cat gct atg ctt ggt gca      1680
```

```
Lys Leu Gly Pro Val Gln Tyr Glu Gly Asn His Ala Met Leu Gly Ala
545                 550                 555                 560 cag agt cct caa aaa tca att tca gaa caa aca gct tat gaa att gat    1728
Gln Ser Pro Gln Lys Ser Ile Ser Glu Gln Thr Ala Tyr Glu Ile Asp
                565                 570                 575 gaa gag gtt cgt tca tta tta aat gag gca cga aat aaa gct gct gaa    1776
Glu Glu Val Arg Ser Leu Leu Asn Glu Ala Arg Asn Lys Ala Ala Glu
                580                 585                 590 att att cag tca aat cgt gaa act cac aag tta att gca gaa gca tta    1824
Ile Ile Gln Ser Asn Arg Glu Thr His Lys Leu Ile Ala Glu Ala Leu
                595                 600                 605 ttg aaa tac gaa aca ttg gat agt aca caa att aaa gct ctt tac gaa    1872
Leu Lys Tyr Glu Thr Leu Asp Ser Thr Gln Ile Lys Ala Leu Tyr Glu
                610                 615                 620 aca gga aag atg cct gaa gca gta gaa gag gaa tct cat gca cta tcc    1920
Thr Gly Lys Met Pro Glu Ala Val Glu Glu Glu Ser His Ala Leu Ser
625                 630                 635                 640 tat gat gaa gta aag tca aaa atg aat gac gaa aaa taa                1959
Tyr Asp Glu Val Lys Ser Lys Met Asn Asp Glu Lys
                645                 650

<210> SEQ ID NO 2
<211> LENGTH: 652
<212> TYPE: PRT
<213> ORGANISM: Streptococcus pneumoniae

<400> SEQUENCE: 2

Met Lys Lys Gln Asn Asn Gly Leu Ile Lys Asn Pro Phe Leu Trp Leu
 1               5                  10                  15

Leu Phe Ile Phe Phe Leu Val Thr Gly Phe Gln Tyr Phe Tyr Ser Gly
                20                  25                  30

Asn Asn Ser Gly Gly Ser Gln Gln Ile Asn Tyr Thr Glu Leu Val Gln
            35                  40                  45

Glu Ile Thr Asp Gly Asn Glu Lys Glu Leu Thr Tyr Gln Pro Asn Val
        50                  55                  60

Ser Val Ile Glu Val Ser Gly Val Tyr Lys Asn Pro Lys Thr Ser Lys
65                  70                  75                  80

Glu Gly Thr Gly Ile Gln Phe Phe Thr Pro Ser Val Thr Lys Val Glu
                85                  90                  95

Lys Phe Thr Ser Thr Ile Leu Pro Ala Asp Thr Thr Val Ser Glu Leu
                100                 105                 110

Gln Lys Leu Ala Thr Asp His Lys Ala Glu Val Thr Val Lys His Glu
            115                 120                 125

Ser Ser Ser Gly Ile Trp Ile Asn Leu Leu Val Ser Ile Val Pro Phe
130                 135                 140

Gly Ile Leu Phe Phe Phe Leu Phe Ser Met Met Gly Asn Met Gly Gly
145                 150                 155                 160

Gly Asn Gly Arg Asn Pro Met Ser Phe Gly Arg Ser Lys Ala Lys Ala
                165                 170                 175

Ala Asn Lys Glu Asp Ile Lys Val Arg Phe Ser Asp Val Ala Gly Ala
            180                 185                 190

Glu Glu Glu Lys Gln Glu Leu Val Glu Val Val Glu Phe Leu Lys Asp
        195                 200                 205

Pro Lys Arg Phe Thr Lys Leu Gly Ala Arg Ile Pro Ala Gly Val Leu
    210                 215                 220

Leu Glu Gly Pro Pro Gly Thr Gly Lys Thr Leu Leu Ala Lys Ala Val
225                 230                 235                 240
```

-continued

```
Ala Gly Glu Ala Gly Val Pro Phe Phe Ser Ile Ser Gly Ser Asp Phe
            245                 250                 255

Val Glu Met Phe Val Gly Val Gly Ala Ser Arg Val Arg Ser Leu Phe
            260                 265                 270

Glu Asp Ala Lys Lys Ala Ala Pro Ala Ile Ile Phe Ile Asp Leu Asn
            275                 280                 285

Asp Ala Val Gly Arg Gln Arg Gly Val Gly Leu Gly Gly Gly Asn Asp
            290                 295                 300

Glu Arg Glu Gln Thr Leu Asn Gln Leu Leu Ile Glu Met Asp Gly Phe
305                 310                 315                 320

Glu Gly Asn Glu Gly Ile Ile Val Ile Ala Ala Thr Asn Arg Ser Asp
            325                 330                 335

Val Leu Asp Pro Ala Leu Leu Arg Pro Gly Arg Phe Asp Arg Lys Val
            340                 345                 350

Leu Val Gly Arg Pro Asp Val Lys Gly Arg Glu Ala Ile Leu Lys Val
            355                 360                 365

His Ala Lys Asn Lys Pro Leu Ala Glu Asp Val Asp Leu Lys Leu Val
            370                 375                 380

Ala Gln Gln Thr Pro Gly Phe Val Gly Ala Asp Leu Glu Asn Val Leu
385                 390                 395                 400

Asn Glu Ala Ala Leu Val Ala Ala Arg Arg Asn Lys Ser Ile Ile Asp
            405                 410                 415

Ala Ser Asp Ile Asp Glu Ala Asp Arg Val Ile Ala Gly Pro Ser
            420                 425                 430

Lys Lys Asp Lys Thr Val Ser Gln Lys Glu Arg Glu Leu Val Ala Tyr
            435                 440                 445

His Glu Ala Gly His Thr Ile Val Gly Leu Val Leu Ser Thr Ala Arg
            450                 455                 460

Val Val His Lys Val Thr Ile Val Pro Arg Gly Arg Ala Gly Gly Tyr
465                 470                 475                 480

Met Ile Ala Leu Pro Lys Glu Asp Gln Met Leu Leu Ser Lys Glu Asp
            485                 490                 495

Met Lys Glu Gln Leu Ala Gly Leu Met Gly Gly Arg Val Ala Glu Glu
            500                 505                 510

Ile Ile Phe Asn Val Gln Thr Thr Gly Ala Ser Asn Asp Phe Glu Gln
            515                 520                 525

Ala Thr Gln Met Ala Arg Ala Met Val Thr Glu Tyr Gly Met Ser Glu
            530                 535                 540

Lys Leu Gly Pro Val Gln Tyr Glu Gly Asn His Ala Met Leu Gly Ala
545                 550                 555                 560

Gln Ser Pro Gln Lys Ser Ile Ser Glu Gln Thr Ala Tyr Glu Ile Asp
            565                 570                 575

Glu Glu Val Arg Ser Leu Leu Asn Glu Ala Arg Asn Lys Ala Ala Glu
            580                 585                 590

Ile Ile Gln Ser Asn Arg Glu Thr His Lys Leu Ile Ala Glu Ala Leu
            595                 600                 605

Leu Lys Tyr Glu Thr Leu Asp Ser Thr Gln Ile Lys Ala Leu Tyr Glu
            610                 615                 620

Thr Gly Lys Met Pro Glu Ala Val Glu Glu Ser His Ala Leu Ser
625                 630                 635                 640

Tyr Asp Glu Val Lys Ser Lys Met Asn Asp Glu Lys
            645                 650
```

-continued

```
<210> SEQ ID NO 3
<211> LENGTH: 1959
<212> TYPE: RNA
<213> ORGANISM: Streptococcus pneumoniae
<220> FEATURE:
<221> NAME/KEY: mRNA
<222> LOCATION: (1)..(1959)

<400> SEQUENCE: 3
```

| | | | | | |
|---|---|---|---|---|---|
| augaaaaaac | aaaauaaugg | uuuaauuaaa | aauccuuuuc | uaugguuauu | auuuaucuuu | 60 |
| uuccuuguga | caggauucca | guauuucuau | ucgggaaua | acucaggagg | aagucagcaa | 120 |
| aucaacuaua | cugaguuggu | acaagaaauu | accgaugguua | augaaaaaga | auuaacuuac | 180 |
| caaccaaaug | uuaguguuau | cgaaguuucu | ggugucuaua | aaaauccuaa | aacaaguaaa | 240 |
| gaaggaacag | guauucaguu | uuucacgcca | ucuguuacua | agguagagaa | auuuaccagc | 300 |
| acuauucuuc | cugcagauac | uaccguauca | gaauugcaaa | aacuugcuac | ugaccauaaa | 360 |
| gcagaaguaa | cuguuaagca | ugaaguuca | aguguauau | ggauuaaucu | acucguaucc | 420 |
| auugugccau | uuggaauucu | auucuucuuc | cuauucucua | ugaugggaaa | uagggagga | 480 |
| ggcaauggcc | guaauccaau | gaguuuugga | cguaguaagg | cuaaagcagc | aaauaaagaa | 540 |
| gauauuaaag | uaagauuuuc | agauguugcu | ggagcugagg | aagaaaaaca | agaacuaguu | 600 |
| gaaguuguug | agucuuaaa | agaccaaaa | cgauucacaa | aacuuggagc | ccguauucca | 660 |
| gcagguguuc | uuuuggaggg | accuccgggg | acaggaaga | cuuugcuugc | uaaggcaguc | 720 |
| gcuggagaag | caggguguucc | auucuuuagu | aucucagguu | cugacuuugu | agaaauguuu | 780 |
| gucggaguug | gagcuagucg | uguucgcucu | cuuuuugagg | augccaaaaa | agcagcacca | 840 |
| gcuaucaucu | uuaucgaucu | aaaugaugcu | guuggacguc | aacguggagu | cggucucggc | 900 |
| ggagguaaug | acgaacguga | acaaaccuug | aaccaacuuu | ugauugagau | ggaugguuuu | 960 |
| gagggaaaug | aagggauuau | cgucaucgcu | gcgacaaacc | guucagaugu | acuugauccu | 1020 |
| gcccuuuugc | guccaggacg | uuuugauaga | aaaguauugg | uuggccgucc | ugauguuaaa | 1080 |
| ggucgugaag | caaucuugaa | aguucacgcu | aagaacaagc | cuuuagcaga | agauguugau | 1140 |
| uugaaauuag | uggcucaaca | aacuccaggc | uuuguuggug | cugauuuaga | gaaugucuug | 1200 |
| aaugaagcag | cuuuaguugc | ugcucgucgc | aauaaaucga | uaauugaugc | uucagauauu | 1260 |
| gaugaagcag | aagauagagu | uauugcggga | ccuucuaaga | aagauaagac | aguuucacaa | 1320 |
| aaagaacgag | aauugguugc | uuaccaugag | gcaggacaua | ccauuguugg | ucuagucuug | 1380 |
| ucgacugcuc | gcguugucca | uaagguuaca | auuguaccac | gcggccgugc | aggcggauac | 1440 |
| augauugcac | uuccuaaaga | ggaucaaaug | cuucuaucua | aagaagauau | gaaagagcaa | 1500 |
| uuggcuggcu | uaaugggugg | acguguagcu | gaagaaauua | ucuuuaaugu | ccaaacuaca | 1560 |
| ggagcuucaa | acgacuuuga | acaagcgaca | caaauggcac | gugcaauggu | uacagaguac | 1620 |
| gguaugagug | aaaaacuugg | cccaguacaa | uaugaaggaa | accaugcuau | gcuuggugca | 1680 |
| cagaguccuc | aaaaaucaau | ucagaacaa | acagcuuaug | aaauugauga | agaguucgu | 1740 |
| ucauuauuaa | augaggcacg | aaauaaagcu | gcugaaauua | uucagucaaa | ucgugaaacu | 1800 |
| cacaaguuaa | uugcagaagc | auuauugaaa | uacgaaacau | uggauaguac | acaaauuaaa | 1860 |
| gcucuuuacg | aaacaggaaa | gaugccugaa | gcaguagaag | aggaaucuca | ugcacuaucc | 1920 |
| uaugaugaag | uaaagucaaa | aaugaaugac | gaaaaauaa | | | 1959 |

```
<210> SEQ ID NO 4
```

<211> LENGTH: 5919
<212> TYPE: DNA
<213> ORGANISM: Streptococcus pneumoniae

<400> SEQUENCE: 4

```
tcgattcgtg gagcaggaaa tcttttagga aaatcccagt ctggtttcat tgattctgtt      60
ggttttgaat tgtattcgca gttattagag gaagctattg ctaaacgaaa cggtaatgct     120
aacgctaaca caagaaccaa agggaatgct gagttgattt tgcaaattga tgcctatctt     180
cctgatactt atatttctga tcaacgacat aagattgaaa tttacaagaa aattcgtcaa     240
attgacaacc gtgtcaatta tgaagagtta caagaggagt tgatagaccg ttttggagaa     300
tacccagatg tagtagccta tcttttagag attggtttgg tcaaatcata cttggacaag     360
gtctttgttc aacgtgtgga agaaaagat aataaaatta caattcaatt tgaaaaagtc     420
actcaacgac tgttttagc tcaagattat tttaaagctt tatccgtaac gaacttaaaa     480
gcaggcatcg ctgagaataa gggattaatg gagcttgtat ttgatgtcca aaataagaaa     540
gattatgaaa ttttagaagg tctgctgatt tttggagaaa gtttattaga gataaaagag     600
tctaaggaaa aaaattccat tgatatttt tcttctataa aatagataaa atggtacaat     660
aataaattga ggtaataagg atgagattag ataaatattt aaaagtatcg cgaattatca     720
agcgtcgtac agtcgcaaag gaagtagcag ataaaggtag aatcaaggtt aatggaatct     780
tggccaaaag ttcaacggac ttgaaagtta atgaccaagt gaaatcgctt ggcaataagt     840
tgctgcttgt aaaggtacta gagatgaaag atagtacaaa aaaagaagat gcagcaggaa     900
tgtatgaaat tatcagtgaa acacgggtag aagaaaatgt ctaaaaatat tgtacaattg     960
aataattctt ttattcaaaa tgaataccaa cgtcgtcgct acctgatgaa agaacgacaa    1020
aaacggaatc gttttatggg aggggtattg attttgatta tgctattatt tatcttgcca    1080
acttttaatt tagcgcagag ttatcagcaa ttactccaaa gacgtcagca attagcagac    1140
ttgcaaactc agtatcaaac tttgagtgat gaaaaggata aggagacagc atttgctacc    1200
aagttgaaag atgaagatta tgctgctaaa tatacacgag cgaagtacta ttattctaag    1260
tcgagggaaa aagtttatac gattcctgac ttgcttcaaa ggtgataaaa tggaaaattt    1320
attagacgta atagagcaat ttttgagttt gtcagatgaa aagctggaag aattggctga    1380
taaaaatcaa ttattgcgtt acaagaaga aaggaaagg aagaatgcgt aaattcttaa    1440
ttattttgtt gctaccaagt tttttgacca tttcaaaagt cgttagcaca gaaaaagaag    1500
tcgtctatac ttcgaaagaa atttattacc tttcacaatc tgactttggt atttattta    1560
gagaaaaatt aagttctccc atggtttatg gagaggttcc tgtttatgcg aatgaagatt    1620
tagtagtgga atctgggaaa ttgactccca aaacaagttt tcaaataacc gagtggcgct    1680
taaataaaca aggaattcca gtatttaagc tatcaaatca tcaatttata gctgcggaca    1740
aacgattttt atatgatcaa tcagaggtaa ctccaacaat aaaaaagta tggttagaat    1800
ctgactttaa actgtacaat agtccttatg atttaaaaga agtgaaatca tccttatcag    1860
cttattcgca gtatcaatc gacaagacca tgtttgtaga aggaagagaa tttctacata    1920
ttgatcaggc tggatgggta gctaaagaat caacttctga agaagataat cggatgagta    1980
aagttcaaga aatgttatct gaaaaatatc agaaagattc tttctctatt tatgttaagc    2040
aactgactac tggaaaagaa gctggtatca atcaagatga aaagatgtat gcagccagcg    2100
ttttgaaact ctcttatctc tattatacgc aagaaaaaaa taaatgaggg tctttatcag    2160
ttagatacga ctgtaaaata cgtatctgca gtcaatgatt ttccaggttc ttataaacca    2220
```

```
gagggaagtg gtagtcttcc taaaaaagaa gataataaag aatattctttt aaaggattta   2280 attacgaaag tatcaaaaga atctgataat gtagctcata atctattggg atattacatt   2340
tcaaaccaat ctgatgccac attcaaatcc aagatgtctg ccattatggg agatgattgg   2400
gatccaaaag aaaaattgat ttcttctaag atggccggga agtttatgga agctatttat   2460
aatcaaaatg gatttgtgct agagtctttg actaaaacag attttgatag tcagcgaatt   2520
gccaaaggtg tttctgttaa agtagctcat aaaattggag atgcggatgg atttaagcat   2580
gatacgggtg ttgtctatgc agatcctcca tttattcttt ctattttcac taagaattct   2640
gattatgata cgatttctaa gatagccaag gatgtttatg aggttctaaa atgagggaac   2700 cagattttt aaatcatttt ctcaagaagg gatatttcaa aaagcatgct aaggcggttc    2760
tagctctttc tggtggatta gattccatgt ttctatttaa ggtattgtct acttatcaaa   2820
aagagttaga gattgaattg attctagctc atgtgaatca taagcagaga attgaatcag   2880
attgggaaga aaaggaatta aggaagttgg ctgctgaagc agagcttcct atttatatca   2940 gcaattttc aggagaattt tcagaagcgc gtgcacgaaa ttttcgttat gatttttttc   3000
aagaggtcca tgaaaaagac aggtgcgaca gctttagtca ctgcccacca tgctgatgat   3060
caggtggaaa cgattttat gcgcttgatt cgaggaacct ccttgcgcta tctatcagga    3120
attaaggaga agcaagtagt cggagagata gaaatcattc gtcccttctt gcattttcag   3180
aaaaaagact ttccatcaat ttttcacttt gaagatacat caaatcagga gaatcattat   3240
tttcgaaatc gtattcgaaa ttcttactta ccagaattgg aaaaagaaaa tcctcgattt   3300
agggatgcaa tccttaggca ttggcaatga aattttagat tatgatttgg caatagctga   3360
attatctaac aatattaatg tggaagattt acagcagtta ttttcttact ctgagtctac   3420
acaaagagtt ttacttcaaa cttatctgaa tcgttttcca gatttgaatc ttacaaaagc   3480
tcagtttgct gaagttcagc agattttaaa atttaaaagc cagtatcgtc atccgattaa   3540
aaatggctat gaattgataa aagagtacca acagtttcag atttgtaaaa tcagtccgca   3600
ggctgatgaa aaggaagatg aacttgtgtt acactatcaa aatcaggtag cttatcaagg   3660
atatttattt tcttttggac ttccattaga aggtgaatta attcaacaaa tacctgtttc   3720
acgtgaaaca tccatacaca ttcgtcatcg aaaaacagga gatgttttga ttaaaaatgg   3780
gcatagaaaa aaactcagac gtttattat tgatttgaaa atccctatgg aaaagagaaa   3840
ctctgctctt attattgagc aatttggtga aattgtctca attttgggaa ttgcgaccaa   3900
taatttgagt aaaaaaacga aaatgatat aatgaacact gtactttata tagaaaaaat   3960
agataggtaa aaatgttag aaaacgatat taaaaagtc ctcgtttcac acgatgaaat    4020
tacagaagca gctaaaaaac taggtgctca attaactaaa gactatgcag gaaaaaatcc   4080
aatcttagtt gggattttaa aaggatctat tcctttatg gctgaattgg tcaaacatat    4140
tgatacacat attgaaatgg acttcatgat ggtttctagc taccatggtg gaacagcaag   4200
tagtggtgtt atcaatatta aacaagatgt gactcaagat atcaaaggaa gacatgttct   4260
atttgtagaa gatatcattg atacaggtca aactttgaag aatttgcgag atatgtttaa   4320
agaaagagaa gcagcttctg ttaaaattgc aaccttgttg gataaaccag aaggacgtgt   4380
tgtagaaatt gaggcagact atacctgctt tactatccca aatgagtttg tagtaggtta   4440
tggtttagac tacaaagaaa attatcgtaa tcttccttat attggagtat tgaaagagga   4500
agtgtattca aattagaaag aataatcttt aatgaaaaaa caaaataatg gtttaattaa   4560
```

```
aaatcctttt ctatggttat tatttatctt tttccttgtg acaggattcc agtatttcct    4620
attctgggaa taactcagga ggaagtcagc aaatcaacta tactgagttg gtacaagaaa    4680
ttaccgatgg taatgtaaaa gaattaactt accaaccaaa tggtagtgtt tcgaagtttc    4740
tggtgtctat aaaaatccta aaacaagtaa agaaggaaca ggtattcagt ttttcacgcc    4800
atctgttact aaggtagaga aatttaccag cactattctt cctgcagata ctaccgtatc    4860
agaattgcaa aaacttgcta ctgaccataa agcagaagta actgttaagc atgaaagttc    4920
aagtggtata tggattaatc tactcgtatc cattgtgcca tttggaattc tattcttctt    4980
cctattctct atgatgggaa atatgggagg aggcaatggc cgtaatccaa tgagttttgg    5040
acgtagtaag gctaaagcag caaataaaga agatattaaa gtaagattt  cagatgttgc    5100 tggagctgag gaagaaaaac aagaactagt tgaagttgtt gagttcttaa aagatccaaa    5160
acgattcaca aaacttggag cccgtattcc agcaggtgtt cttttggagg gacctccggg    5220
gacaggtaag actttgcttg ctaaggcagt cgctggagaa gcaggtgttc cattctttag    5280
tatctcaggt tctgactttg tagaaatgtt tgtcggagtt ggagctagtc gtgttcgctc    5340 tcttttgag gatgccaaaa aagcagcacc agctatcatc tttatcgact gaaatggatg    5400
cccgtgggac gtcaacgtgg agtcggtctc ggcggaggta atgacgaacg tgaacaaacc    5460
ttgaaccaac ttttgattga gatggatggt tttgagggaa atgaagggat tatcgtcatc    5520
gctgcgacaa accgttcaga tgtacttgat cctgcccttt tgcgtccagg acgttttgat    5580
agaaaagtat tggttggccg tcctgatgtt aaaggtcgtg aagcaatctt gaaagttcac    5640
gctaagaaca agccttttagc agaagatgtt gatttgaaat tagtggctca acaaactcca    5700
ggctttgttg gtgctgattt agagaatgtc ttgaatgaag cagctttagt tgctgctcgt    5760
cgcaataaat cgataattga tgcttcagat atgatgaaag cagaagatag agttattgct    5820
ggaccttcta agaaagataa gacagtttca caaaaagaac gagaattggt tgcttaccat    5880
gaggcaggac ataccattgt tggtctagtc ttgtcgact                           5919
```

STREPOCOCCUS PNEUMONIAE GENE SEQUENCE FTSH

This application claims the benefit of U.S. Provisional Application No. 60/036,281, filed Dec. 13, 1996.

BACKGROUND OF THE INVENTION

This invention provides isolated DNA sequences, proteins encoded thereby, and methods of using said DNA and protein in a variety of applications.

Widespread antibiotic resistance in common pathogenic bacterial species has justifiably alarmed the medical and research communities. Frequently, resistant organisms are co-resistant to several antibacterial agents. Penicillin resistance in *Streptococcus pneumoniae* has been particularly problematic. This organism causes upper respiratory tract infections. Modification of a penicillin-binding protein (PBP) underlies resistance to penicillin in the majority of cases. Combating resistance to antibiotic agents will require research into the molecular biology of pathogenic organisms. The goal of such research will be to identify new antibacterial agents.

While researchers continue to develop antibiotics effective against a number of microorganisms, *Streptococcus pneumoniae* has been more refractory. In part, this is because *Streptococcus pneumoniae* is highly recombinogenic and readily takes up exogenous DNA from its surroundings. Thus, there is a need for new antibacterial compounds and new targets for antibacterial therapy in *Streptococcus pneumoniae*.

BRIEF SUMMARY OF THE INVENTION

The present invention relates to an isolated gene and encoded protein from *S. pneumoniae*. The invention enables: (1) preparation of probes and primers for use in hybridizations and PCR amplifications, (2) production of proteins and RNAs encoded by said gene and related nucleic acids, and (3) methods to identify compounds that bind and/or inhibit said protein(s).

In one embodiment the present invention relates to an isolated nucleic acid molecule encoding FtsH protein.

In another embodiment, the invention relates to a nucleic acid molecule comprising the nucleotide sequence identified as SEQ ID NO:1, SEQ ID NO:3, or SEQ ID NO:4.

In another embodiment, the present invention relates to a nucleic acid that encodes SEQ ID NO:2.

In another embodiment the present invention relates to an isolated protein molecule, wherein said protein molecule comprises the sequence identified as SEQ ID NO:2.

In yet another embodiment, the present invention relates to a recombinant DNA vector that incorporates the FtsH gene in operable linkage to gene expression sequences enabling the gene to be transcribed and translated in a host cell.

In still another embodiment the present invention relates to host cells that have been transformed or transfected with the cloned FtsH gene such that said gene is expressed in the host cell.

This invention also provides a method of determining whether a nucleic acid sequence of the present invention, or fragment thereof, is present in a sample, comprising contacting the sample, under suitable hybridization conditions, with a nucleic acid probe of the present invention.

In a still further embodiment, the present invention relates to a method for identifying compounds that bind and/or inhibit the FtsH protein.

DETAILED DESCRIPTION OF THE INVENTION

"ORF" (i.e. "open reading frame") designates a region of genomic DNA beginning with a Met or other initiation codon and terminating with a translation stop codon, that potentially encodes a protein product. "Partial ORF" means a portion of an ORF as disclosed herein such that the initiation codon, the stop codon, or both are not disclosed.

"Consensus sequence" refers to an amino acid or nucleotide sequence that may suggest the biological function of a protein, DNA, or RNA molecule. Consensus sequences are identified by comparing proteins, RNAs, and gene homologues from different species.

The terms "cleavage" or "restriction" of DNA refers to the catalytic cleavage of the DNA with a restriction enzyme that acts only at certain sequences in the DNA (viz. sequence-specific endonucleases). The various restriction enzymes used herein are commercially available and their reaction conditions, cofactors, and other requirements are used in the manner well known to one of ordinary skill in the art. Appropriate buffers and substrate amounts for particular restriction enzymes are specified by the manufacturer or can readily be found in the literature.

"Essential genes" or "essential ORFs" or "essential proteins" refer to genomic information or the protein(s) or RNAs encoded thereby, that when disrupted by knockout mutation, or by other mutation, result in a loss of viability of cells harboring said mutation.

"Non-essential genes" or "non-essential ORFs" or "non-essential proteins" refer to genomic information or the protein(s) or RNAs encoded therefrom which when disrupted by knockout mutation, or other mutation, do not result in a loss of viability of cells harboring said mutation.

"Minimal gene set" refers to a genus comprising about 256 genes conserved among different bacteria such as *M. genitalium* and *H. influenzae*. The minimal gene set may be necessary and sufficient to sustain life. See e.g. A. Mushegian and E. Koonin, "A minimal gene set for cellular life derived by comparison of complete bacterial genomes" Proc. Nat. Acad. Sci. 93, 10268–273 (1996).

"Knockout mutant" or "knockout mutation" as used herein refers to an in vitro engineered disruption of a region of native chromosomal DNA, typically within a protein coding region, such that a foreign piece of DNA is inserted within the native sequence. A knockout mutation occurring in a protein coding region prevents expression of the wild-type protein. This usually leads to loss of the function provided by the protein. A "knockout cassette" refers to a fragment of native chromosomal DNA having cloned therein a foreign piece of DNA that may provide a selectable marker.

The term "plasmid" refers to an extrachromosomal genetic element. The starting plasmids herein are either commercially available, publicly available on an unrestricted basis, or can be constructed from available plasmids in accordance with published procedures. In addition, equivalent plasmids to those described are known in the art and will be apparent to the ordinarily skilled artisan.

"Recombinant DNA cloning vector" as used herein refers to any autonomously replicating agent, including, but not limited to, plasmids and phages, comprising a DNA molecule to which one or more additional DNA segments can or have been added.

The term "recombinant DNA expression vector" as used herein refers to any recombinant DNA cloning vector, for example a plasmid or phage, in which a promoter and other regulatory elements are present to enable transcription of the inserted DNA.

The term "vector" as used herein refers to a nucleic acid compound used for introducing exogenous DNA into host cells. A vector comprises a nucleotide sequence which may encode one or more protein molecules. Plasmids, cosmids, viruses, and bacteriophages, in the natural state or which have undergone recombinant engineering, are examples of commonly used vectors.

The terms "complementary" or "complementarity" as used herein refer to the capacity of purine and pyrimidine nucleotides to associate through hydrogen bonding to form double stranded nucleic acid molecules. The following base pairs are related by complementarity: guanine and cytosine; adenine and thymine; and adenine and uracil. As used herein, "complementary" applies to all base pairs comprising two single-stranded nucleic acid molecules. "Partially complementary" means one of two single-stranded nucleic acid molecules is shorter than the other, such that one of the molecules remains partially single-stranded.

"Oligonucleotide" refers to a short nucleotide chain comprising from about 2 to about 25 nucleotides.

"Isolated nucleic acid compound" refers to any RNA or DNA sequence, however constructed or synthesized, which is locationally distinct from its natural location.

A "primer" is a nucleic acid fragment which functions as an initiating substrate for enzymatic or synthetic elongation of, for example, a nucleic acid molecule.

The term "promoter" refers to a DNA sequence which directs transcription of DNA to RNA.

A "probe" as used herein is a labeled nucleic acid compound which can be used to hybridize with another nucleic acid compound.

The term "hybridization" or "hybridize" as used herein refers to the process by which a single-stranded nucleic acid molecule joins with a complementary strand through nucleotide base pairing.

"Substantially purified" as used herein means a specific isolated nucleic acid or protein, or fragment thereof, in which substantially all contaminants (i.e. substances that differ from said specific molecule) have been separated from said nucleic acid or protein. For example, a protein may, but not necessarily, be "substantially purified" by the IMAC method as described herein.

"Selective hybridization" refers to hybridization under conditions of high stringency. The degree of hybridization between nucleic acid molecules depends upon, for example, the degree of complementarity, the stringency of hybridization, and the length of hybridizing strands.

The term "stringency" relates to nucleic acid hybridization conditions. High stringency conditions disfavor non-homologous base pairing. Low stringency conditions have the opposite effect. Stringency may be altered, for example, by changes in temperature and salt concentration. Typical high stringency conditions comprise hybridizing at 50° C. to 65° C. in 5× SSPE and 50% formamide, and washing at 50° C. to 65° C. in 0.5× SSPE; typical low stringency conditions comprise hybridizing at 35° C. to 37° C. in 5× SSPE and 40% to 45% formamide and washing at 42° C. in 1×–2× SSPE.

"SSPE" denotes a hybridization and wash solution comprising sodium chloride, sodium phosphate, and EDTA, at pH 7.4. A 20× solution of SSPE is made by dissolving 174 g of NaCl, 27.6 g of NaH$_2$PO4.H$_2$O, and 7.4 g of EDTA in 800 ml of H$_2$O. The pH is adjusted with NaOH and the volume brought to 1 liter.

"SSC" denotes a hybridization and wash solution comprising sodium chloride and sodium citrate at pH 7. A 20× solution of SSC is made by dissolving 175 g of NaCl and 88 g of sodium citrate in 800 ml of H$_2$O. The volume is brought to 1 liter after adjusting the pH with 10N NaOH.

The FtsH gene disclosed herein (SEQ ID NO:1) and related nucleic acids (e.g. SEQ ID NO:3 and SEQ ID NO:4) encode an essential integral membrane protein of 70.7 kDa that has an AAA-type ATPase domain at its C-terminus. FtsH is involved in degradation of the heat-shock transcription factor sigma 32.

The proteins categorized as "minimal gene set" counterparts are homologous to a set of highly conserved proteins found in other bacteria. The minimal gene set proteins are thought to be essential for viability and are useful targets for the development of new antibacterial compounds.

In one embodiment, the proteins of this invention are purified, and used in a screen to identify compounds that bind and/or inhibit the activity of said proteins. A variety of suitable screens are contemplated for this purpose. For example, the protein(s) can be labeled by known techniques, such as radiolabeling or fluorescent tagging, or by labeling with biotin/avidin. Thereafter, binding of a test compound to a labeled protein can be determined by any suitable means, well known to the skilled artisan.

Skilled artisans will recognize that the DNA molecules of this invention, or fragments thereof, can be generated by general cloning methods. PCR amplification using oligonucleotide primers targeted to any suitable region of SEQ ID NO:1 is preferred. Methods for PCR amplification are widely known in the art. See e.g. *PCR Protocols: A Guide to Method and Application,* Ed. M. Innis et al., Academic Press (1990) or U.S. Pat. No. 4,889,818, which hereby is incorporated by reference. A PCR comprises DNA, suitable enzymes, primers, and buffers, and is conveniently carried out in a DNA Thermal Cycler (Perkin Elmer Cetus, Norwalk, Conn.). A positive PCR result is determined by, for example, detecting an appropriately-sized DNA fragment following agarose gel electrophoresis.

The DNAs of the present invention may also be produced using synthetic methods well known in the art. (See, e.g., E. L. Brown, R. Belagaje, M. J. Ryan, and H. G. Khorana, *Methods in Enzymology,* 68:109–151 (1979)). An apparatus such as the Applied Biosystems Model 380A or 380B DNA synthesizers (Applied Biosystems, Inc., 850 Lincoln Center Drive, Foster City, Calif. 94404) may be used to synthesize DNA. Synthetic methods rely upon phosphotriester chemistry [See, e.g., M. J. Gait, ed., *Oligonucleotide Synthesis, A Practical Approach,* (1984)], or phosphoramidite chemistry.

Protein Production Methods

The present invention relates further to substantially purified proteins encoded by the gene disclosed herein.

Skilled artisans will recognize that proteins can be synthesized by different methods, for example, chemical methods or recombinant methods, as described in U.S. Pat. No. 4,617,149, which hereby is incorporated by reference.

The principles of solid phase chemical synthesis of polypeptides are well known in the art and may be found in general texts relating to this area. See, e.g., H. Dugas and C. Penney, *Bioorganic Chemistry* (1981) Springer-Verlag, New York, 54–92. Peptides may be synthesized by solid-phase methodology utilizing an Applied Biosystems 430A peptide synthesizer (Applied Biosystems, Foster City, Calif.) and synthesis cycles supplied by Applied Biosystems. Protected amino acids, such as t-butoxycarbonyl-protected amino acids, and other reagents are commercially available from many chemical supply houses.

The proteins of the present invention can also be made by recombinant DNA methods. Recombinant methods are preferred if a high yield is desired. Recombinant methods involve expressing the cloned gene in a suitable host cell. The gene is introduced into the host cell by any suitable means, well known to those skilled in the art. While chromosomal integration of the cloned gene is within the scope of the present invention, it is preferred that the cloned gene be maintained extra-chromosomally, as part of a vector in which the gene is in operable-linkage to a promoter.

Recombinant methods can also be used to overproduce a membrane-bound or membrane-associated protein. In some cases, membranes prepared from recombinant cells expressing such proteins provide an enriched source of the protein.
Expressing Recombinant Proteins in Procaryotic and Eucaryotic Host Cells Procaryotes are generally used for cloning DNA sequences and for constructing vectors. For example, the *Escherichia coli* K12 strain 294 (ATCC No. 31446) is particularly useful for expression of foreign proteins. Other strains of *E. coli*, bacilli such as *Bacillus subtilis,* enterobacteriaceae such as *Salmonella typhimurium* or *Serratia marcescans,* various Pseudomonas species may also be employed as host cells in cloning and expressing the recombinant proteins of this invention. Also contemplated are various strains of Streptococcus and Streptocmyces.

For effective recombinant protein production, a gene must be linked to a promoter sequence. Suitable bacterial promoters include b -lactamase [e.g. vector pGX2907, ATCC 39344, contains a replicon and b -lactamase gene], lactose systems [Chang et al., *Nature* (London), 275:615 (1978); Goeddel et al., *Nature* (London), 281:544 (1979)], alkaline phosphatase, and the tryptophan (trp) promoter system [vector pATH1 (ATCC 37695)] designed for the expression of a trpE fusion protein. Hybrid promoters such as the tac promoter (isolatable from plasmid pDR540, ATCC-37282) are also suitable. Promoters for use in bacterial systems also will contain a Shine-Dalgarno sequence, operably linked to the DNA encoding the desired polypeptides. These examples are illustrative rather than limiting.

A variety of mammalian cells and yeasts are also suitable hosts. The yeast *Saccharomyces cerevisiae* is commonly used. Other yeasts, such as *Kluyveromyces lactis,* are also suitable. For expression of recombinant genes in Saccharomyces, the plasmid YRp7 (ATCC-40053), for example, may be used. See, e.g., L. Stinchcomb, et al., *Nature,* 282:39 (1979); J. Kingsman et al., *Gene,* 7:141 (1979); S. Tschemper et al., Gene, 10:157 (1980). Plasmid YRp7 contains the TRP1 gene, a selectable marker for a trp1 mutant.
Purification of Recombinantly-Produced Protein An expression vector carrying a nucleic acid or gene of the present invention is transformed or transfected into a suitable host cell using standard methods. Cells that contain the vector are propagated under conditions suitable for expression of a recombinant protein. For example, if the gene is under the control of an inducible promoter, then suitable growth conditions would incorporate the appropriate inducer. The recombinantly-produced protein may be purified from cellular extracts of transformed cells by any suitable means.

In a preferred process for protein purification a gene is modified at the 5' end, or at some other position, such that the encoded protein incorporates several histidine residues (viz. "histidine tag"). This "histidine tag" enables "immobilized metal ion affinity chromatography" (IMAC), a single-step protein purification method described in U.S. Pat. No. 4,569,794, which hereby is incorporated by reference. The IMAC method enables isolation of substantially pure protein starting from a crude cellular extract.

As skilled artisans will recognize, owing to the degeneracy of the code, the proteins of the invention can be encoded by a large genus of different nucleic acid sequences. This invention further comprises said genus.

The ribonucleic acid compounds of the invention may be prepared using the polynucleotide synthetic methods discussed supra, or they may be prepared enzymatically using RNA polymerase to transcribe a DNA template.

The most preferred systems for preparing the ribonucleic acids of the present invention employ the RNA polymerase from the bacteriophage T7 or the bacteriophage SP6. These RNA polymerases are highly specific, requiring the insertion of bacteriophage-specific sequences at the 5' end of a template. See, J. Sambrook, et al., supra, at 18.82–18.84.

This invention also provides nucleic acids that are complementary to the sequences disclosed herein.

The present invention also provides probes and primers, useful for a variety of molecular biology techniques including, for example, hybridization screens of genomic or subgenomic libraries, or detection and quantification of mRNA species as a means to analyze gene expression. A nucleic acid compound is provided comprising any of the sequences disclosed herein, or a complementary sequence thereof, or a fragment thereof, which is at least 15 base pairs in length, and which will hybridize selectively to *Streptococcus pneumoniae* DNA or mRNA. Preferably, the 15 or more base pair compound is DNA. A probe or primer length of at least 15 base pairs is dictated by theoretical and practical considerations. See e.g. B. Wallace and G. Miyada, "Oligonucleotide Probes for the Screening of Recombinant DNA Libraries," In *Methods in Enzymology,* Vol. 152, 432–442, Academic Press (1987).

The probes and primers of this invention can be prepared by methods well known to those skilled in the art (See e.g. Sambrook et al. supra). In a preferred embodiment the probes and primers are synthesized by the polymerase chain reaction (PCR).

The present invention also relates to recombinant DNA cloning vectors and expression vectors comprising the nucleic acids of the present invention. Preferred nucleic acid vectors are those that comprise DNA. The skilled artisan understands that choosing the most appropriate cloning vector or expression vector depends on the availability of restriction sites, the type of host cell into which the vector is to be transfected or transformed, the purpose of transfection or transformation (e.g., stable transformation as an extrachromosomal element, or integration into a host chromosome), the presence or absence of readily assayable or selectable markers (e.g., antibiotic resistance and metabolic markers of one type and another), and the number of gene copies desired in the host cell.

Suitable vectors comprise RNA viruses, DNA viruses, lytic bacteriophages, lysogenic bacteriophages, stable bacteriophages, plasmids, viroids, and the like. The most preferred vectors are plasmids.

Host cells harboring the nucleic acids disclosed herein are also provided by the present invention. A preferred host is *E. coli* transfected or transformed with a vector comprising a nucleic acid of the present invention.

The invention also provides a host cell capable of expressing a gene described herein, said method comprising transforming or otherwise introducing into a host cell a recombinant DNA vector comprising an isolated DNA sequence that encodes said gene. The preferred host cell is any strain of E. coli that can accommodate high level expression of an exogenously introduced gene. Transformed host cells are cultured under conditions well known to skilled artisans, such that said gene is expressed, thereby producing the encoded protein in the recombinant host cell.

To discover compounds having antibacterial activity, one can look for agents that inhibit cell growth and/or viability by, for example, inhibiting enzymes required for cell wall biosynthesis, and/or by identifying agents that interact with membrane proteins. A method for identifying such compounds comprises contacting a suitable protein or membrane preparation with a test compound and monitoring by any suitable means an interaction and/or inhibition of a protein of this invention.

For example, the instant invention provides a screen for compounds that interact with the proteins of the invention, said screen comprising:

a) preparing FtsH protein, or membranes enriched in said protein;

b) exposing said protein or membranes to a test compound; and c) detecting an inhibition of the enzymatic activity of said protein with said compound by any suitable means.

The screening method of this invention may be adapted to automated procedures such as a PANDEX® (Baxter-Dade Diagnostics) system, allowing for efficient high-volume screening of compounds.

In a typical screen, protein is prepared as described herein, preferably using recombinant DNA technology. A test compound is introduced into a reaction vessel containing said protein. The reaction/interaction of said protein and said compound is monitored by any suitable means, for example by monitoring the loss in enzymatic activity. Several suitable assays for FtsH activity are known, for example, the generation of ADP and $^{32}P_i$ starting from γ-$^{32}$PATP substrate. Alternatively one may detect the degradation of known FtsH substrates, such as sigma 32 from E. coli, or SpoVM from B. subtilis. Still other suitable assays include the detection of FtsH protease activity against suitable peptide substrates. [See generally, EMBO J. 14, 2551, 1995; J. Bact. 179, 5534, 1997; J. Bact. 175, 1344, 1993 all of which are hereby incorporated by reference].

In such a screening protocol FtsH is prepared as described herein, preferably using recombinant DNA technology. A test compound is introduced into a reaction vessel containing the FtsH protein or fragment thereof. Binding of FtsH by a test compound is determined by any suitable means. For example, in one method radioactively-labeled or chemically-labeled test compound may be used. Binding of the protein by the compound is assessed, for example, by quantifying bound label versus unbound label using any suitable method. Binding of a test compound may also be carried out by a method disclosed in U.S. Pat. No. 5,585,277, which hereby is incorporated by reference. In this method, binding of a test compound to a protein is assessed by monitoring the ratio of folded protein to unfolded protein, for example by monitoring sensitivity of said protein to a protease, or amenability to binding of said protein by a specific antibody against the folded state of the protein.

The foregoing screening methods are useful for identifying a ligand of a FtsH protein, perhaps as a lead to a pharmaceutical compound for modulating the state of differentiation of an appropriate tissue. A ligand that binds FtsH, or related fragment thereof, is identified, for example, by combining a test ligand with FtsH under conditions that cause the protein to exist in a ratio of folded to unfolded states. If the test ligand binds the folded state of the protein, the relative amount of folded protein will be higher than in the case of a test ligand that does not bind the protein. The ratio of protein in the folded versus unfolded state is easily determinable by, for example, susceptibility to digestion by a protease, or binding to a specific antibody, or binding to chaperonin protein, or binding to any suitable surface.

The following examples more fully describe the present invention. Those skilled in the art will recognize that the particular reagents, equipment, and procedures described are merely illustrative and are not intended to limit the present invention in any manner.

EXAMPLE 1

Production of a Vector for Expressing S. pneumoniae FtsH in a Host Cell

An expression vector suitable for expressing S. pneumoniae FtsH in a variety of procaryotic host cells, such as E. coli, is easily made. The vector contains an origin of replication (Ori), an ampicillin resistance gene (Amp) useful for selecting cells which have incorporated the vector following a tranformation procedure, and further comprises the T7 promoter and T7 terminator sequences in operable linkage to the FtsH coding region. Plasmid pET11A (obtained from Novogen, Madison, Wis.) is a suitable parent plasmid. pET11A is linearized by restriction with endonucleases NdeI and BamHI. Linearized pET11A is ligated to a DNA fragment bearing NdeI and BamHI sticky ends and comprising the coding region of the S. pneumoniae FtsH (SEQ ID NO:1). The coding region for FtsH is easily produced by PCR technology using suitably designed primers to the ends of the coding region specified in SEQ ID NO:1.

The FtsH encoding nucleic acid used in this construct is slightly modified at the 5' end (amino terminus of encoded protein) in order to simplify purification of the encoded protein product. For this purpose, an oligonucleotide encoding 8 histidine residues is inserted after the ATG start codon. Placement of the histidine residues at the amino terminus of the encoded protein serves to enable the IMAC one-step protein purification procedure.

EXAMPLE 2

Recombinant Expression and Purification of a Protein Encoded by S. pneumoniae FtsH An expression vector that carries FtsH from the S. pneumoniae genome as disclosed herein and which FtsH is operably-linked to an expression promoter is transformed into E. coli BL21 (DE3) (hsdS gal lcIts857 ind1Sam7nin5lacUV5-T7gene 1) using standard methods (see Example 4). Transformants, selected for resistance to ampicillin, are chosen at random and tested for the presence of the vector by agarose gel electrophoresis using quick plasmid preparations. Colonies which contain the vector are grown in L broth and the protein product encoded by the vector-borne ORF is purified by immobilized metal ion affinity chromatography (IMAC), essentially as described in U.S. Pat. No. 4,569,794.

Briefly, the IMAC column is prepared as follows. A metal-free chelating resin (e.g. Sepharose 6B IDA, Pharmacia) is washed in distilled water to remove preservative substances and infused with a suitable metal ion [e.g. Ni(II), Co(II), or Cu(II)] by adding a 50 mM metal chloride or metal sulfate aqueous solution until about 75% of the interstitial spaces of the resin are saturated with colored metal ion. The column is then ready to receive a crude cellular extract containing the recombinant protein product.

After removing unbound proteins and other materials by washing the column with any suitable buffer, pH 7.5, the bound protein is eluted in any suitable buffer at pH 4.3, or preferably with an imidizole-containing buffer at pH 7.5.

What is claimed is:

1. An isolated nucleic acid fragment encoding a protein having the amino acid sequence that is SEQ ID NO:2.

2. An isolated nucleic acid fragment, wherein said fragment has a sequence selected from the group consisting of:
    (a) SEQ ID NO:1;
    (b) SEQ ID NO:3;
    (c) a nucleic acid fragment complementary to (a) or (b); and
    (d) a nucleic acid fragment that encodes the same genetic information as (a), (b), or (c), but which is degenerate in accordance with the degeneracy of the genetic code.

3. An isolated nucleic acid fragment, wherein said fragment has a sequence specified herein as SEQ ID NO:4.

4. An isolated nucleic acid fragment of claim 2 wherein the sequence of said fragment is selected from the group consisting of SEQ ID NO:1, a sequence complementary to SEQ ID NO:1, and a nucleic acid fragment that encodes the same genetic information as either of the foregoing, but which is degenerate in accordance with the degeneracy of the genetic code.

5. An isolated nucleic acid fragment of claim 2 wherein the sequence of said fragment is selected from the group consisting of SEQ ID NO:3, a sequence complementary to SEQ ID NO:3, and a nucleic acid fragment that encodes the same genetic information as either of the foregoing, but which is degenerate in accordance with the degeneracy of the genetic code.

6. An isolated nucleic acid fragment that hybridizes to SEQ ID NO:1 or SEQ ID NO:3 under high stringency conditions and that encodes a protein having *Streptococcus pneumoniae* FtsH activity.

7. A vector comprising an isolated nucleic acid fragment of claim 2.

8. A vector, as in claim 7, wherein said isolated nucleic acid fragment is SEQ ID NO:1, operably-linked to a promoter sequence.

9. A host cell containing a vector of claim 7.

10. A host cell containing a vector of claim 8.

11. A method for constructing a recombinant host cell having the potential to express SEQ ID NO:2, said method comprising introducing into said host cell by any suitable means a vector of claim 8.

12. A method for expressing SEQ ID NO:2 in a recombinant host cell of claim 10, said method comprising culturing said recombinant host cell under conditions suitable for gene expression.

13. An isolated nucleic acid fragment of claim 6, wherein said FtsH activity is selected from the group consisting of FtsH enzymatic activity and FtsH ligand binding.

14. An isolated nucleic acid fragment of claim 13, wherein said FtsH enzymatic activity is one or more activity selected from the group consisting of ATPase activity, degradation of heat-shock transcription factor sigma 32 from *E. coli,* degradation of SpoVM from *B. subtilis,* and FtsH protease activity.

16. A method for producing a protein having the amino acid sequence which is SEQ ID NO:2 in a recombinant host cell of claim 10, said method comprising culturing said recombinant host cell under conditions suitable for gene expression, and recovering said protein.

16. An isolated nucleic acid fragment consisting of a nucleotide sequence encoding a protein having the amino acid sequence that is SEQ ID NO:2.

17. An isolated nucleic acid fragment, wherein said fragment consists of a sequence selected from the group consisting of:

(a) SEQ ID NO:1;

(b) SEQ ID NO:3;

(c) a nucleic acid fragment complementary to (a) or b); and (d) a nucleic acid fragment that encodes the same genetic information as (a), (b), or (c), but which is degenerate in accordance with the degeneracy of the genetic code.

18. An isolated nucleic fragment, wherein said fragment consists of a sequence specified herein as SEQ ID NO:4.

19. An isolated nucleic acid fragment of claim 17 wherein the sequence of said fragment is selected from the group consisting of:

(a) SEQ ID NO:1;

(b) a sequence complementary to SEQ ID NO:1; and (c) a nucleic acid fragment that encodes the same genetic information as (a) or (b), but which is degenerate in accordance with the degeneracy of the genetic code.

20. An isolated nucleic acid fragment of claim 17 wherein the sequence of said fragment is selected from the group consisting of:

(a) SEQ ID NO:3;

(b) a sequence complementary to SEQ ID NO:3; and (c) a nucleic acid fragment that encodes the same genetic information as (a) or (b), but which is degenerate in accordance with the degeneracy of the genetic code.

21. A vector comprising an isolated nucleic acid fragment of claim 17.

22. A vector as in claim 21, wherein said isolated nucleic acid fragment is SEQ ID NO:1, operably-linked to a promoter sequence.

23. A host cell containing a vector of claim 21.

24. A host cell containing a vector of claim 22.

25. A method for constructing a recombinant host cell having the potential to express SEQ ID NO:2, said method comprising introducing into said host cell by any suitable means a vector of claim 22.

26. A method for expressing SEQ ID NO:2 in a recombinant host cell of claim 24, said method comprising culturing said recombinant host cell under conditions suitable for gene expression.

27. A method for producing a protein having the amino acid sequence which is SEQ ID NO:2 in a recombinant host cell of claim 24, said method comprising culturing said recombinant host cell under conditions suitable for gene expression, and recovering said protein.

* * * * *